(12) United States Patent
Nakano et al.

(10) Patent No.: US 7,101,716 B2
(45) Date of Patent: Sep. 5, 2006

(54) FORMALDEHYDE DETECTING MATERIAL

(75) Inventors: Nobuo Nakano, Tokyo (JP); Tetsuya Kawabe, Tokyo (JP); Yasuhiro Terauchi, Tokyo (JP); Kouzi Suzuki, Yokohama (JP)

(73) Assignee: Riken Keiki Co., Ltd., Tokyo (JP)

( * ) Notice: Subject to any disclaimer, the term of this patent is extended or adjusted under 35 U.S.C. 154(b) by 0 days.

(21) Appl. No.: 10/658,754

(22) Filed: Sep. 10, 2003

(65) Prior Publication Data
US 2004/0197225 A1 Oct. 7, 2004

(30) Foreign Application Priority Data
Sep. 10, 2002 (JP) .............................. 2002-263713

(51) Int. Cl.
*G01N 33/00* (2006.01)
(52) U.S. Cl. .................. 436/128; 436/164; 436/169; 422/55; 422/56; 422/57; 422/58; 422/83
(58) Field of Classification Search ............... 436/128, 436/164, 169; 422/55, 56, 57, 58, 83
See application file for complete search history.

(56) References Cited

U.S. PATENT DOCUMENTS

| | | | | |
|---|---|---|---|---|
| 3,635,677 A | * | 1/1972 | Drake et al. | 436/60 |
| 4,489,164 A | * | 12/1984 | McConnaughey et al. | 436/130 |
| 4,511,658 A | * | 4/1985 | Lambert et al. | 436/130 |
| 4,666,859 A | * | 5/1987 | Attar | 436/130 |
| 4,844,867 A | * | 7/1989 | Bather | 422/60 |

FOREIGN PATENT DOCUMENTS

| | | |
|---|---|---|
| JP | H07-55792 | 3/1995 |
| JP | H07-229889 | 8/1995 |

OTHER PUBLICATIONS

Akiba et al. Ring Transformation Equilibrium (Bond Switch) in the 5-2(-Aminovinyl)isothiazole System via Hypervalent Sulfurane, Synthesis, Structure Development, and Kinetic Study, J. Am. Chem. Soc, 1985, 107, 2721-2730.*

* cited by examiner

Primary Examiner—Monique T. Cole
(74) Attorney, Agent, or Firm—Connolly, Bove, Lodge & Hutz, LLP

(57) ABSTRACT

A detecting material to detect formaldehyde at low concentration in the atmosphere in a short time is prepared by impregnating a base material containing at least silica gel with a coloring liquid containing 4-amino-4-phenyl-3-ene-2-one and a buffer solution and volatilizing the solvent.

16 Claims, 5 Drawing Sheets

FORMALDEHYDE DETECTING MATERIAL

FIELD OF THE INVENTION

This invention relates to a detecting material for detecting formaldehyde present in environment by color reaction.

DESCRIPTION OF THE PRIOR ART

As concern about environmental health grows recently, much consideration is given to indoor environmental pollution by formaldehyde. Formaldehyde contained in building materials of newly built houses and furniture is considered as a cause of various symptoms in those who are anaphylactic to chemical substances that are generically called the sick house symptom.

It may seem possible that use of reagents can be eliminated by saturating filter paper or other porous carriers with reagents. However, such test papers do not have high enough detection sensitivity. Their background color is too great, dynamic range is too low and detection range is too narrow for determination of reaction colors by optical densitometer etc. Besides, colors of such test papers are likely to be changed by other gases than formaldehyde as well. These problems make such test papers unsuitable for practical uses.

To solve these problems, Japanese Provisional Patent Publication No. H07-55792, for example, proposes a formaldehyde detecting paper comprising acid salt of hydroxylamine and a hydrogen ion concentration indicator changing color in acid region spread over porous carriers.

This detecting paper is capable of detecting such formaldehyde of only a few ppm as remains in environment after disinfection with formaldehyde in special environment with a relative humidity of over 80 percent. Because, however, high humidity is indispensable, measurement range is limited.

To solve this problem, Japanese Provisional Patent Publication No. H07-22989, for example, proposes a detector comprising hydroxylamine sulfate and at least one hydrogen ion concentration indicator selected from the group of methyl yellow, methyl orange, benzyl orange and tropeolin spread over a porous carrier. The degree of coloration by sulfuric acid naturally free on the tape is controlled to improve shelf life.

However, this type of detector has a problem that a long time is required to detect formaldehyde of such concentration as is possessed by the formaldehyde liberated from the wallpaper adhesive, which constitutes a cause of the sick house symptom, into atmosphere.

The object of this invention is to provide a detecting material having high enough sensitivity to detect formaldehyde of such concentration as will constitute a cause of the sick house symptom in a short time.

SUMMARY OF THE INVENTION

A detecting material according to this invention comprises a base material containing a silica gel at least in the gas reaction zone and impregnated with a coloring liquid containing 4-amino-4-phenyl-3-ene-2-one and a buffer solution, with the solvent volatilized.

This detecting material detects formaldehyde with a high sensitivity by detecting the light absorbance of the singular absorbed wavelength of lutidine formed by the reaction of 4-amino-4-phenyl-3-ene-2-one with formaldehyde.

DESCRIPTION OF PREFERRED EMBODIMENTS

Details of this invention are described below by making reference to preferred embodiments.

A coloring liquid is prepared by dissolving 4-amino-4-phenyl-3-ene-2-one and phosphoric acid buffer solution (pH 2.5) in a volatilizable solvent, such as methanol. A detecting material of this invention is made by impregnating a tabular base material containing silica gel at least in the surface thereof with the coloring liquid thus prepared and volatilizing the methanol or other solvent.

The 4-amino-4-phenyl-3-ene-2-one shown in Equation 1 can be prepared as described below.

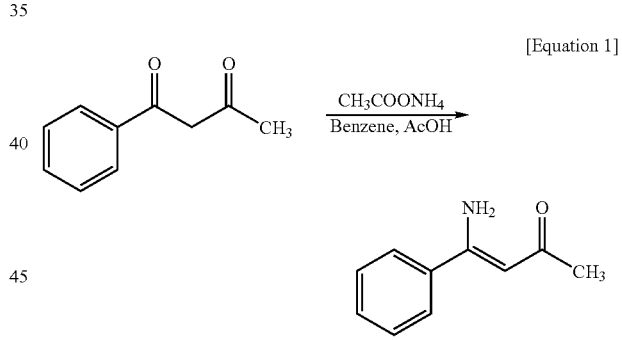

[Equation 1]

3.24R (0.02 mol) of 1-phenyl-1,3-butanedione, 60 ml of dry benzene, 3.08 g (0.04 mol) of ammonium acetate and 1.0 ml of acetic acid were put in a 200 ml three-neck flask having a Dean-Stark trap and circulated for 12 hours in a stream of nitrogen gas. The product was cooled, washed with water and dried with anhydrous sodium sulfate. After removing the solvent under a reduced pressure, the product was purified by column chromatography.

The base material comprises a sheet formed by compressing particles of silica gel, or a sheet formed by forming a layer of silica gel particles at the surface of glass or other base material, or a sheet formed by depositing from a mixture of fibers such as cellulose and silica gel particles.

Figure 5:
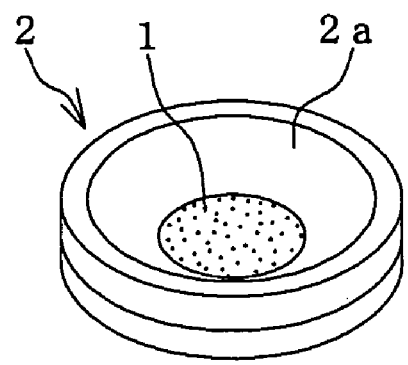
FIGS. 5(a) and 5(b) show an example of the detecting material of this invention and a measuring device using it.
Figure 5:
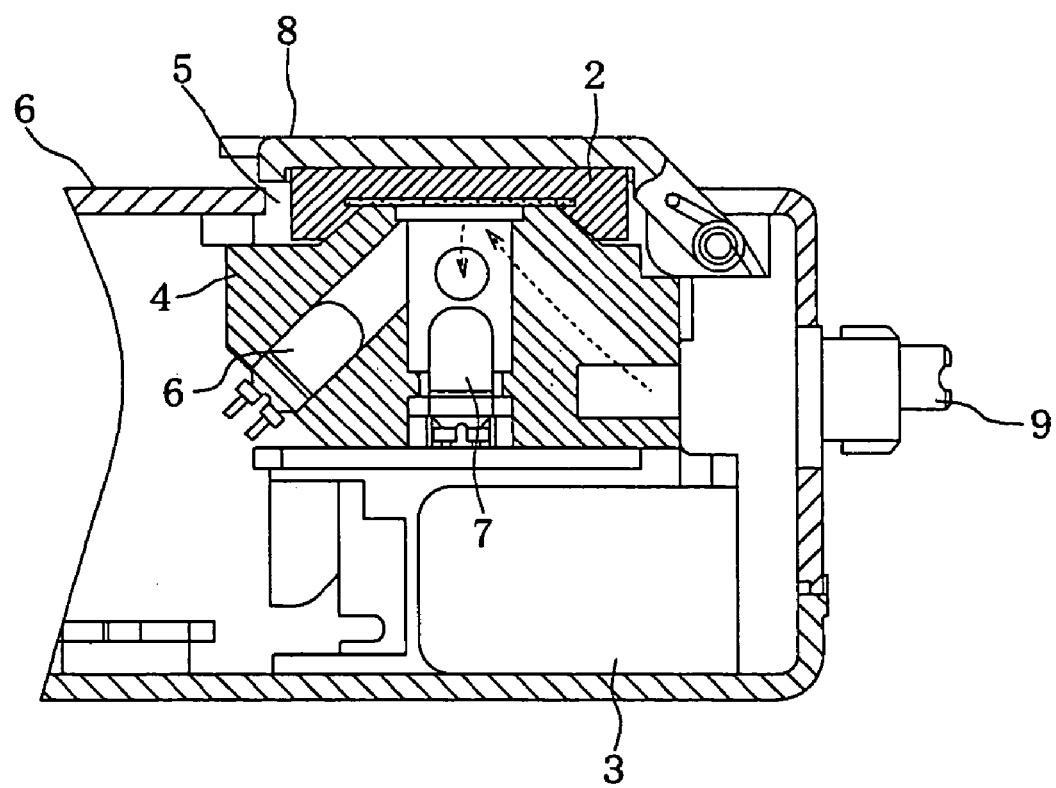

The detecting material 1 forms a unit 2 by mounting in a recess having an opening 2a shown in FIG. 5(a) as disclosed in Japanese Provisional Patent Publication H07-229889. The unit 2 set in a portable detector shown in FIG. 5(b) permits easy detection of formaldehyde.

The detector comprises a gas suction unit 3, measuring head 4, a signal processing unit detecting changes in the optical concentration from the measuring head and a case 6 having a window 5 through which part of the measuring head is exposed. The gas suction unit 3 is adapted to direct the sucked gas to the unit 2. Reference numerals 8 and 9 respectively designate a cover and a gas suction port.

Figure 1:
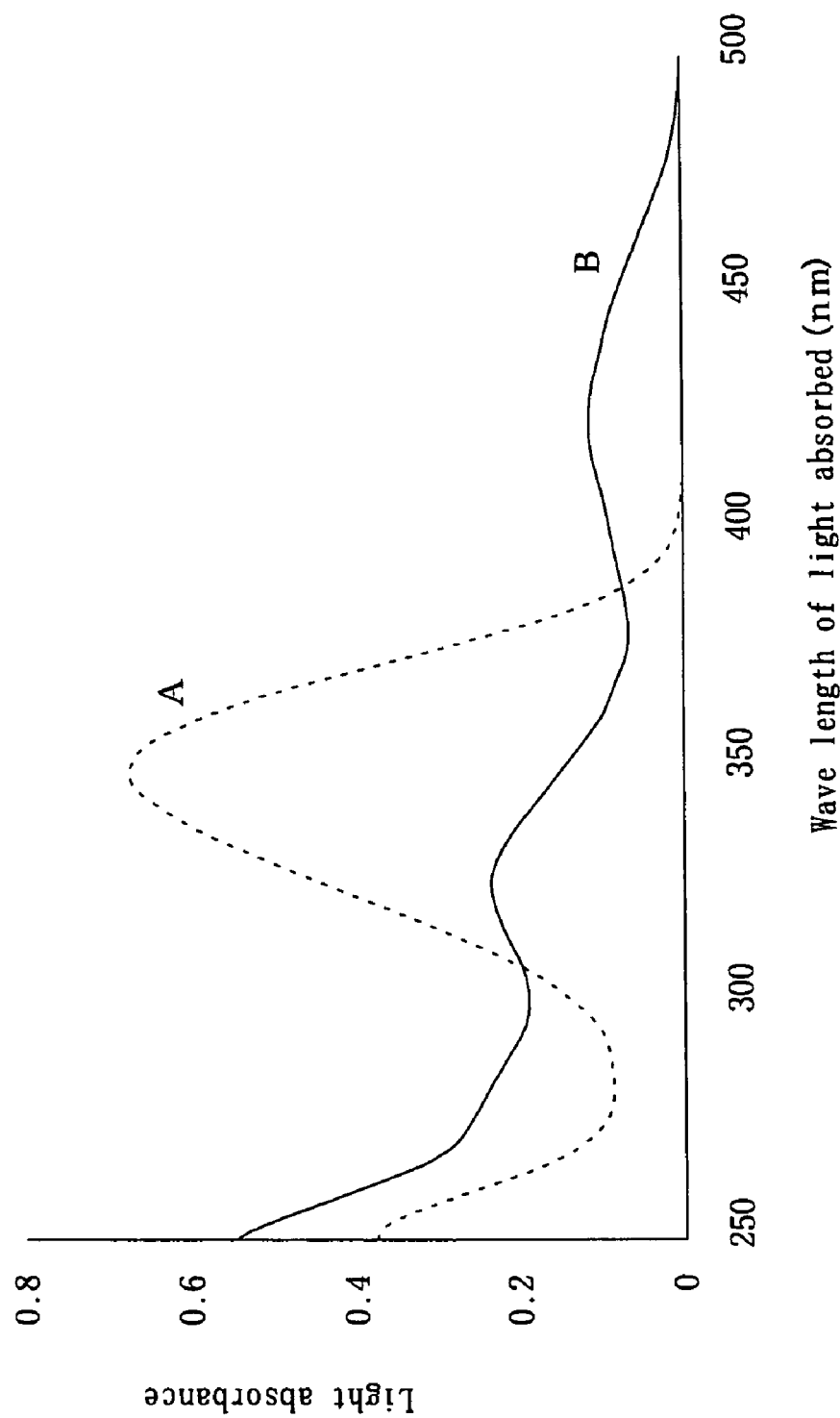
FIG. 1 is a diagram plotting the light absorbance spectra of the coloring reagent itself and the product of reaction of the coloring reagent with formaldehyde.

The gas detecting material thus formed has a light absorption characteristic that the peak is reached at 350 nm and absorption stops at 400 nm as indicated by curve A in FIG. 1.

When the detecting material is set in the measuring device disclosed, for example, in Japanese Provisional Patent Publication No. H07-229889 and exposed to an atmosphere containing formaldehyde, formaldehyde reacts with 4-amino-4-phenyl-3-ene-2-one by catalysis of silica gel particles as shown in Equation 2.

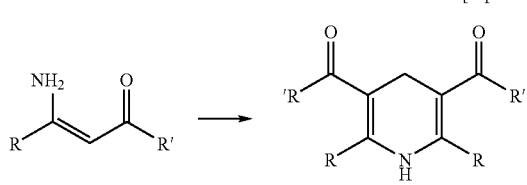

[Equation 2]

The reaction forms a lutidine 1-(5-acetyl-2,4-diphenyl-3H,6H-3-azinyl)ethan-1-one at the surface of the detecting material depending on the concentration of formaldehyde.

The lutidine has an absorption characteristic to respond to wavelengths longer than 400 nm to which 4-amino-4-phenyl-3-ene-2-one does not respond as indicated by curve B in FIG. 1. A photoreceiving means 7 singularly detects the wavelength at, for example, 430 nm by irradiating the light from, for example, a light emitting diode 6.

Figure 2:
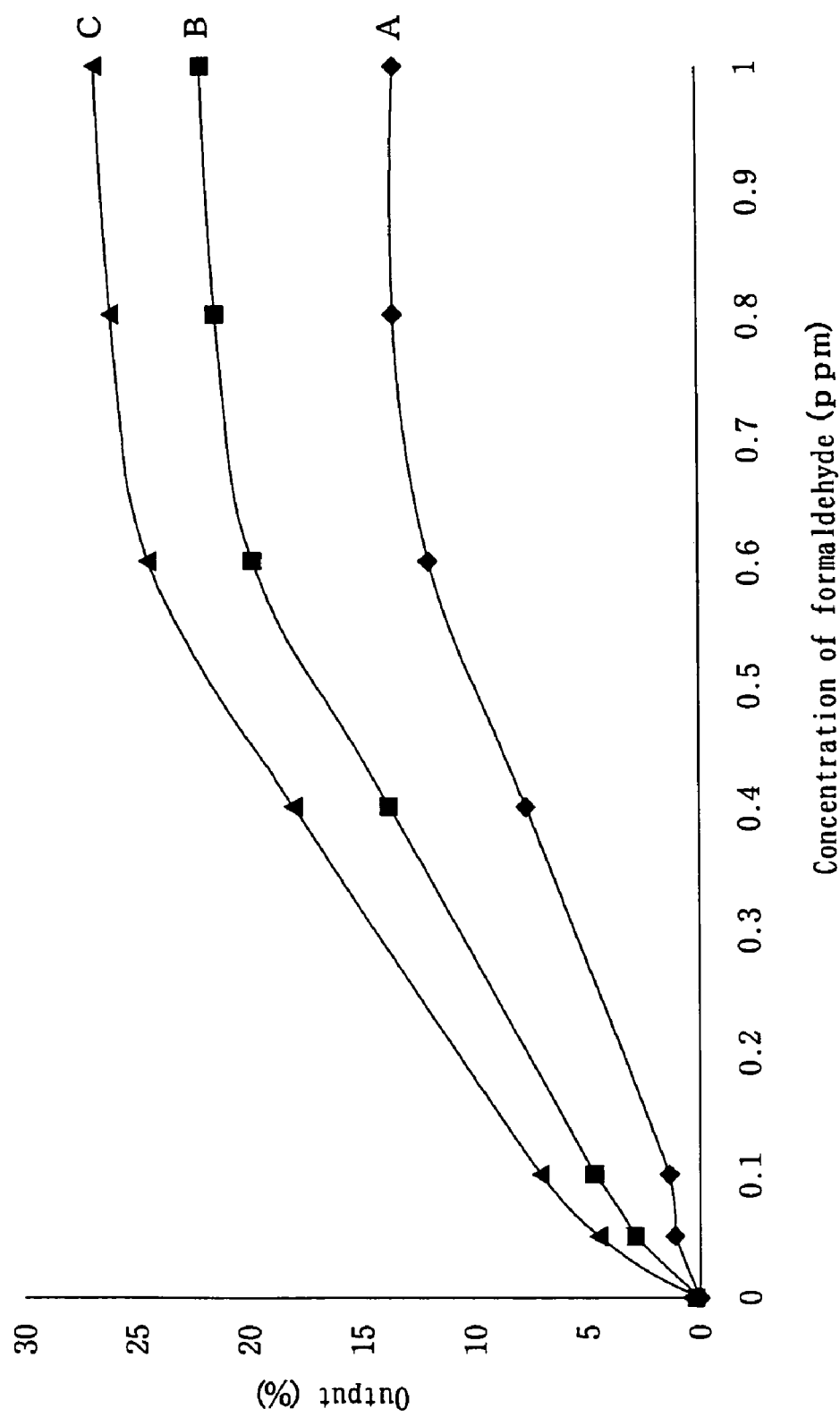
FIG. 2 is a diagram plotting changes in the light absorbance of the detecting material of this invention vs. formaldehyde by using the sampling time as a parameter.

A coloring liquid was prepared by gradually dissolving 1 wt. % of 4-amino-4-phenyl-3-ene-2-one and 20 v/v % of phosphoric acid buffer solution in methanol and a detecting material was prepared by the method described earlier. FIG. 2 shows the results obtained by measuring light absorbance of formaldehyde of different concentrations by setting exposure time (sampling time) at five minutes (indicated by A), ten minutes (indicated by B) and fifteen minutes (indicated by C).

As can be seen, formaldehyde between approximately 0.05 ppm and 0.7 ppm was surely detected.

Figure 3:
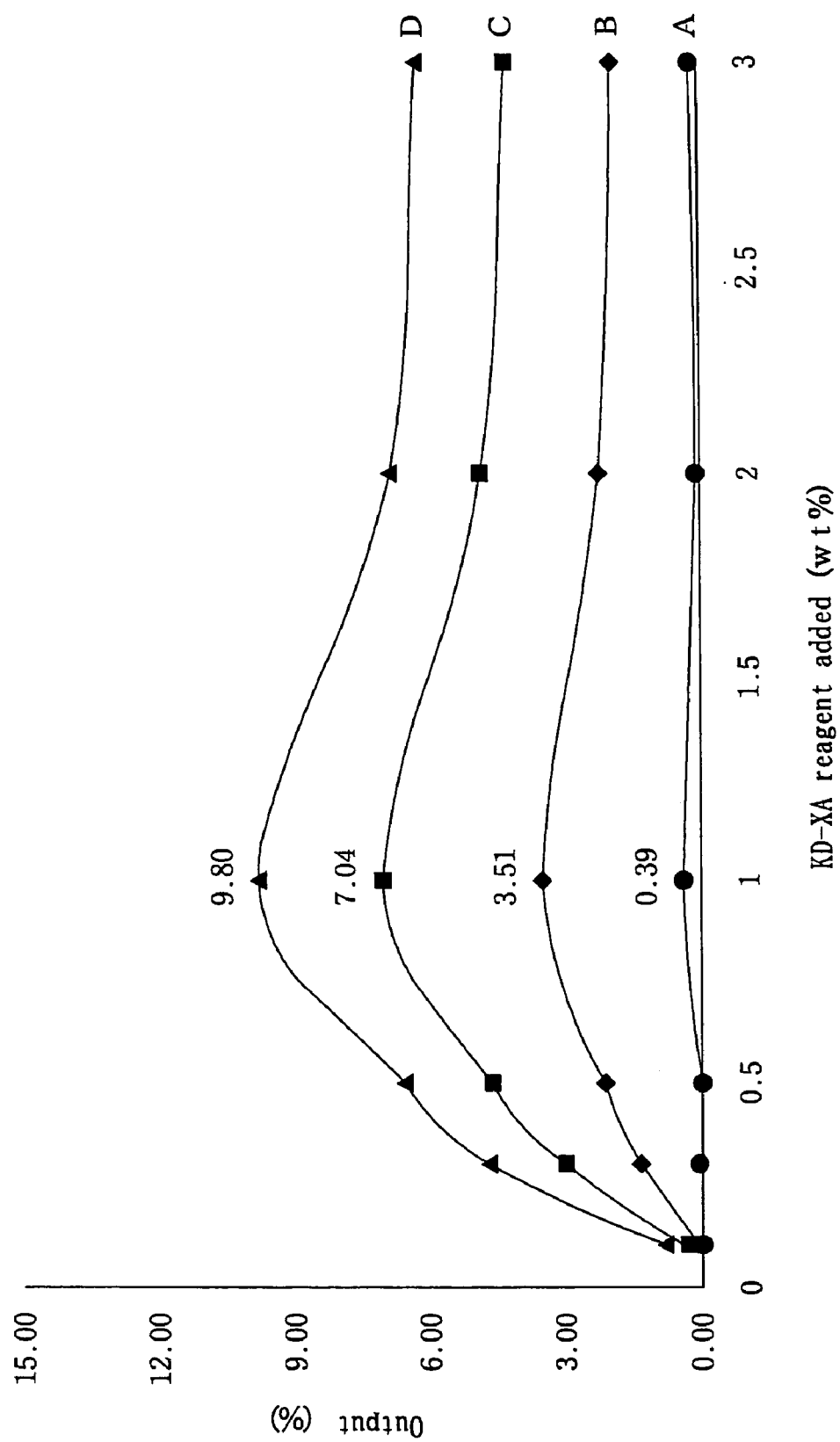
FIG. 3 is a diagram plotting changes in the light absorbance of the detecting material of this invention vs. 4-amino-4-phenyl-3-ene-2-one by using the sampling time as a parameter.

Next, another detecting material was prepared by fixing the concentration of the phosphoric acid buffer solution at 20 v/v % and varying the concentration of 4-amino-4-phenyl-3-ene-2-one. FIG. 3 shows the results obtained by exposing the detecting material thus prepared to air not containing formaldehyde (indicated by A) and one containing formaldehyde for five minutes (indicated by B), ten minutes (indicated by C) and fifteen minutes (indicated by D).

The results showed that the coloring reagent containing 0.5 wt % 4-amino-4-phenyl-3-ene-2-one has the smallest blank value and a high relative sensitivity.

Figure 4:
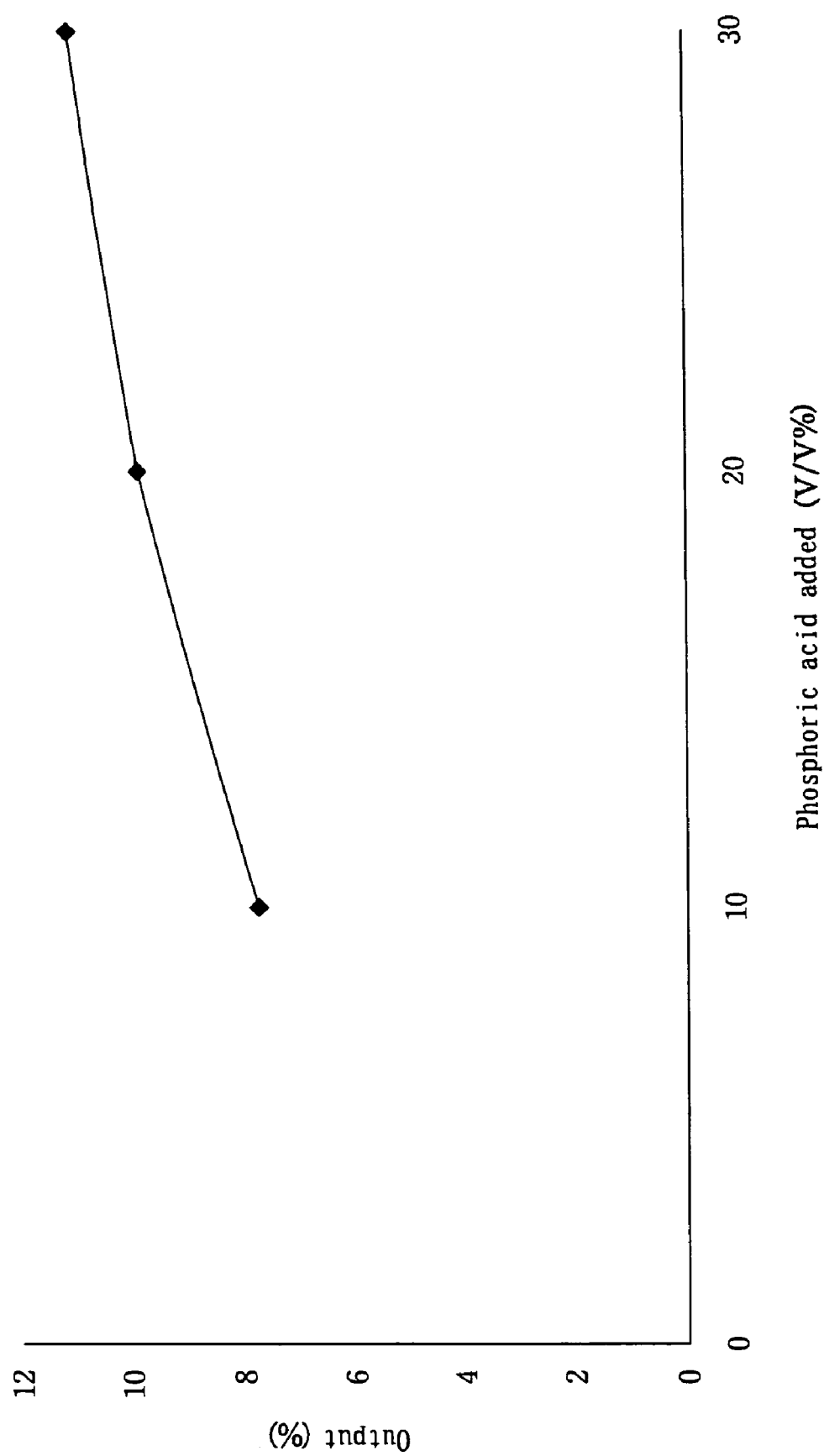
FIG. 4 is a diagram plotting changes in the light absorbance of the detecting material of this invention vs. a buffer solution of phosphoric acid buffer solution.

Still another detecting material was prepared by fixing the concentration of 4-amino-4-phenyl-3-ene-2-one (at 1 wt %) and varying the concentration of the phosphoric acid buffer solution. FIG. 4 shows the sensitivity of the detecting material thus prepared to formaldehyde.

The results showed that the sensitivity of the detecting material is proportional to the concentration of the phosphoric acid buffer solution. Because of drying or other factors, it proved desirable to keep the concentration of the phosphoric acid buffer solution at approximately 10 v/v %.

What is claimed is:

1. A formaldehyde detecting material comprising:
   a tabular base material containing silica gel,
   and having impregnated therein;
   at least in a gas reaction zone a coloring liquid containing 4-amino-4-phenyl-3-ene-2-one and a buffer;
   wherein said gas reaction zone is for reacting said 4-amino-4-phenyl-3-ene-2-one with formaldehyde.

2. A formaldehyde detecting material according to claim 1, wherein said base material comprises a sheet formed by compressing particles of silica gel.

3. A formaldehyde detecting material according to claim 1, in which said base material has a layer of silica gel at the surface thereof.

4. A formaldehyde detecting material according to claim 1, in which said base material comprises a sheet formed by depositing a mixture of fibers and silica gel particles.

5. A formaldehyde detecting material according to claim 1, in which said coloring liquid detecting material contains not less ten 0.5 wt % 4-amino-4-phenyl-3-ene-2-one.

6. A formaldehyde detecting material according to claim 1, in which said buffer is provided by a phosphoric acid buffer solution.

7. A formaldehyde detecting material according to claim 6 wherein said phosphoric acid buffer solution has a concentration of about 10 to 30 v/v %.

8. A formaldehyde detecting material according to claim 6 wherein said phosphoric acid buffer solution has a concentration of about 20 v/v %.

9. A formaldehyde detecting material according to claim 6 wherein said phosphoric acid buffer solution has a concentration of about 10 v/v %.

10. A formaldehyde detecting material according to claim 1 wherein the amount of the 4-amino-4-phenyl-3-ene-2-one is about 0.5 to 3 wt %.

11. A formaldehyde detecting material according to claim 1 wherein the amount of the 4-amino-4-phenyl-3-ene-2-one is about 0.5 wt %.

12. A formaldehyde detecting material according to claim 1 wherein the amount of the 4-amino-4-phenyl-3-ene-2-one is about 1 wt %.

13. A formaldehyde detecting material according to claim 8 wherein the amount of the 4-amino-4-phenyl-3-ene-2-one is about 0.5 to 3 wt %.

14. A formaldehyde detecting material according to claim 8 wherein the amount of the 4-amino-4-phenyl-3-ene-2-one is about 0.5 wt %.

15. A formaldehyde detecting material according to claim 8 wherein the amount of the 4-amino-4-phenyl-3-ene-2-one is about 1 wt %.

16. A formaldehyde detecting material according to claim 9 wherein the amount of the 4-amino-4-phenyl-3-ene-2-one is about 1 wt %.

* * * * *